US00RE34714E

United States Patent [19]

Burns et al.

[11] E Patent Number: Re. 34,714

[45] Reissued Date of Patent: Aug. 30, 1994

[54] CERVICAL COLLAR OF LAMINATE CONSTRUCTION

[76] Inventors: William R. Burns; Gary R. Burns; Paul W. Burns, all of 252 Old Baptist Rd., North Kingstown, R.I. 02852

[21] Appl. No.: 954,560

[22] Filed: Sep. 30, 1992

Related U.S. Patent Documents

Reissue of:

[64] Patent No.: 4,940,043
Issued: Jul. 10, 1990
Appl. No.: 337,418
Filed: Apr. 13, 1989

U.S. Applications:

[63] Continuation-in-part of Ser. No. 943,655, Dec. 17, 1986, abandoned.

[51] Int. Cl.[5] ..... A61F 5/01

[52] U.S. Cl. ..... 602/18; 128/DIG. 23

[58] Field of Search ..... 602/5, 17, 18; 128/DIG. 23

[56] References Cited

U.S. PATENT DOCUMENTS

| | | | |
|---|---|---|---|
| D. 248,872 | 8/1978 | Thomas | 128/DIG. 23 X |
| 2,359,148 | 9/1944 | Partridge | 24/17 AP |
| 3,320,950 | 5/1967 | McElvenny | 128/75 |
| 3,756,226 | 9/1973 | Calabrese et al. | 128/DIG. 23 X |
| 3,819,796 | 6/1974 | Webster et al. | 128/90 X |
| 3,911,497 | 10/1975 | Lewis, Jr. et al. | 128/89 R X |
| 4,060,075 | 11/1977 | Blomer et al. | 128/90 |
| 4,205,667 | 6/1980 | Gaylord | 128/DIG. 23 X |
| 4,217,893 | 8/1980 | Payton | 128/89 R |
| 4,538,597 | 9/1985 | Lerman | 128/75 |
| 4,677,696 | 7/1987 | Calabrese | 128/DIG. 23 X |

*Primary Examiner*—Robert A. Hafer
*Assistant Examiner*—Brian F. Hanlon
*Attorney, Agent, or Firm*—Barlow & Barlow, Ltd.

[57] ABSTRACT

A cervical collar including front and back halves adapted to fit around the neck, and an adjustable strap for releasably securing the halves in position on the neck. The halves of the collar are made from a laminate having outer layers of a foamed polymeric material and an inner layer of a solid, non-foamed thermoplastic material. The foam layes provide padding and comfort, and the solid layers provide rigidity and support to immobilize the head and neck. In one embodiment there is provided a large hole in the front most portion of the collar to accommodate the Adam's apple. In another embodiment, the strap is attached to the back half by looping it through parallel slots formed in the rearmost portion of the collar which are narrower than the width of the strap adjacent the slots, and attached to the front half by stitching at the ends thereof.

1 Claim, 2 Drawing Sheets

CERVICAL COLLAR OF LAMINATE CONSTRUCTION

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation in part of application Ser. No. 06/943,655, filed Dec. 17, 1986 now abandoned.

BACKGROUND OF THE INVENTION

This invention relates to cervical collars worn to immobilize or restrict the movement of the head.

Cervical collars are generally of two types, either stock ("off-the-shelf") in various sizes, or customized ("made-to-fit") for the individual patient. Because of the additional time, equipment and labor involved, the customized collar is less popular than the stock collar which can be made available in different standard sizes to accommodate various heights and circumferences of the neck.

The desirable qualities of a stock cervical collar include comfort, support and durability. Comfort requires that all portions of the collar in contact with the neck be soft and flexible, and also that the collar be lightweight. Support requires a certain amount of rigidity to immobilize the head and neck, with respect to both forward-backward and side-to-side movement. Durability requires that the collar not tear or lose its qualities of comfort and support, or otherwise wear out during a period of use exceeding several weeks or months.

In addition to the foregoing, the ideal cervical collar would be simple and economical to manufacture.

Heretofore, stock cervical collars have failed to meet one or more of these requirements. Exemplary of such prior art collars is that described in U.S. Pat. No. 3,756,226 which is commonly known as the Philadelphia collar. While perhaps the most popular of stock collars, the Philadelphia collar has several drawbacks. The Philadelphia collar has front and back halves made of a foam polymeric material which are held in place by an adjustable strap secured to each half by rivets extending through the foam material. Rigid reinforcing members are positioned vertically at the bight of each half, i.e. under the chin and along the spine at the base of the head. The foam polymeric material does not support the head so that side-to-side movement thereof is not adequately inhibited by the reinforcement added only at the bights. Moreover, the foam material tears easily, especially adjacent the strap. The reinforcement under the chin is uncomfortable because the support of the chin is concentrated on the relatively small area of the reinforcing member in contact with the chest, and also because the reinforcement is secured tightly to the neck against the trachea or Adam's apple.

Other types of prior art cervical collars are seen in U.S. Pat. Nos. 4,205,667; 3,662,057; 3,504,667; 3,042,027; and 2,818,063.

SUMMARY OF THE INVENTION

The present invention is a cervical collar having preformed front and back halves and an adjustable strap for holding the halves in position to encircle the neck. The front and back halves are preformed from a laminate comprising outer layers or sheets of foam polymeric material and an inner layer or sheet of solid or non-foamed thermoplastic material. The foam outer layers provide comfort, while the solid insert provides reinforcement for support and durability. The strap may be secured to the front half of the collar by stitching at ends of the front half, and to the back half by looping through parallel slots formed in the rearmost portion thereof. In this manner, no protrusions or rivets are made to contact the wearer, and all portions of the collar in contact with the wearer are soft and flexible for complete comfort.

In a preferred embodiment, a large hole is formed in the front most portion of the front half to correspond to and accommodate the trachea or Adam's apple.

DESCRIPTION OF THE PREFERRED EMBODIMENTS

Figure 1:
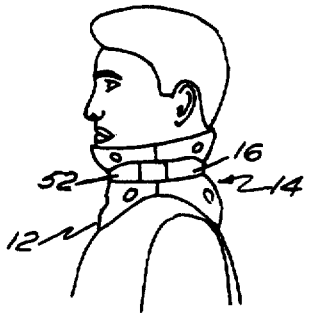
FIG. 1 is a perspective view of the collar in place on a person's neck.
Figure 2:
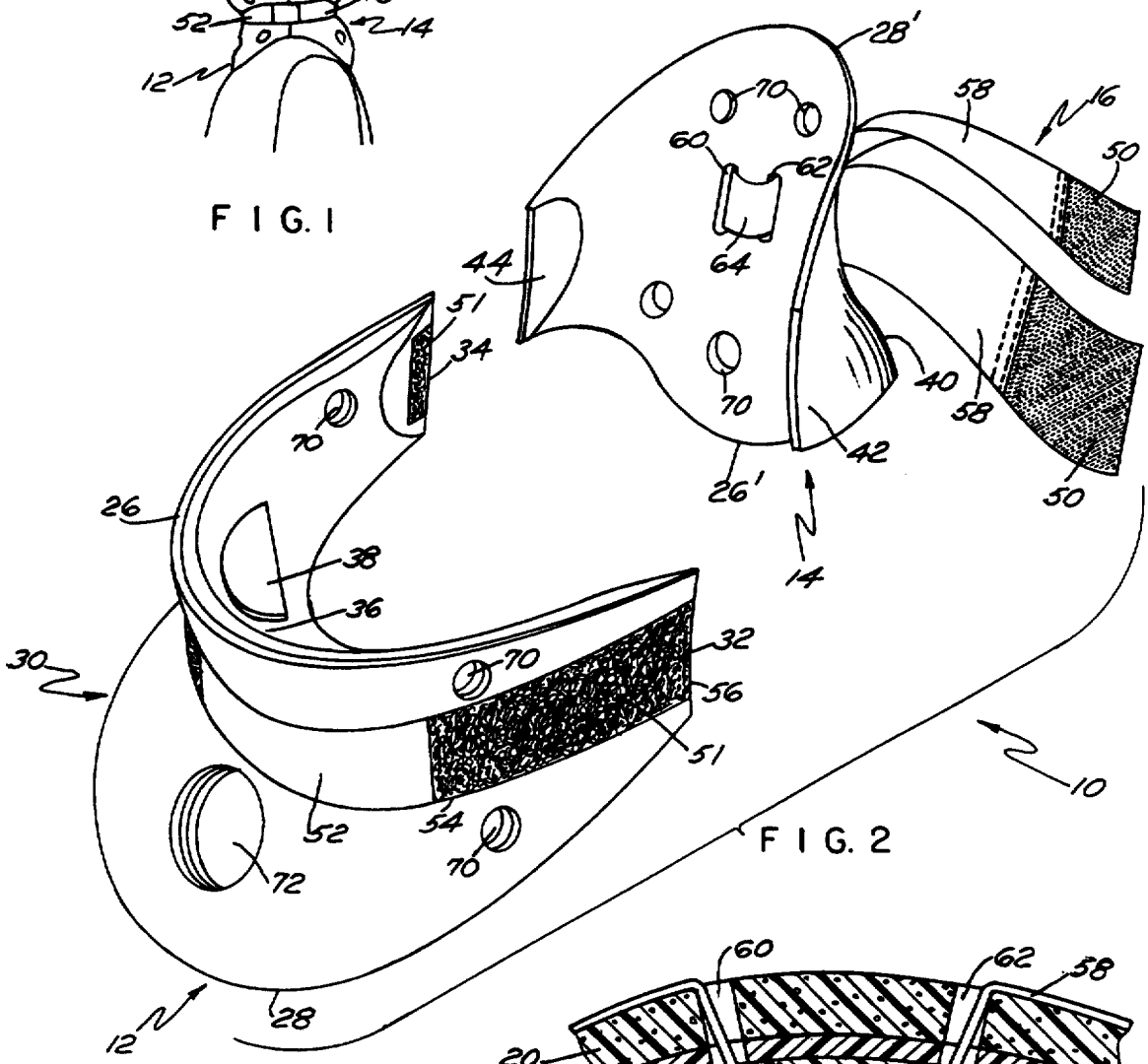
FIG. 2 is a perspective view of the front and back halves of the collar disassembled.
Figure 5:
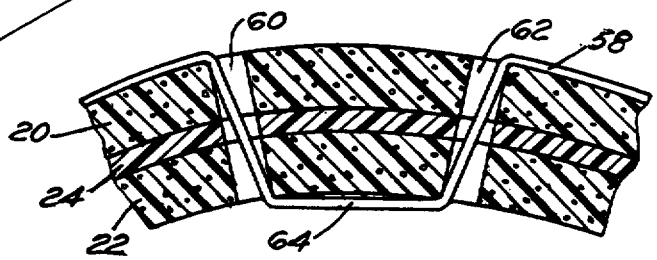
FIG. 5 is a sectional view of the back half of the collar along the lines 5—5 in FIG. 4.
Figure 3:
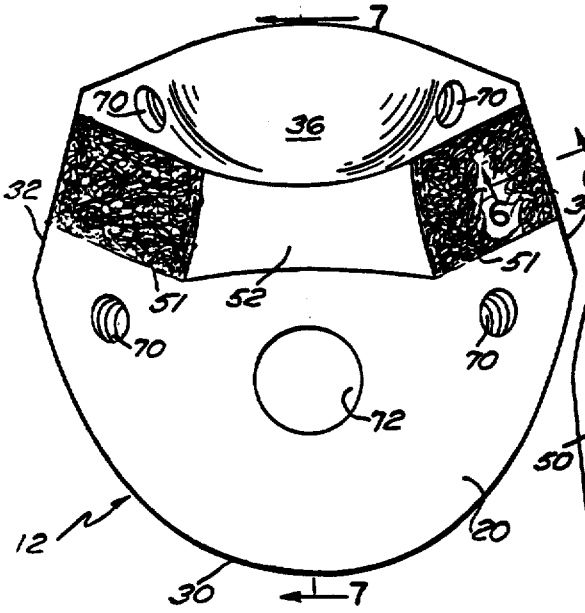
FIG. 3 is a perspective view of the front half of the collar as viewed from the front.
Figure 4:
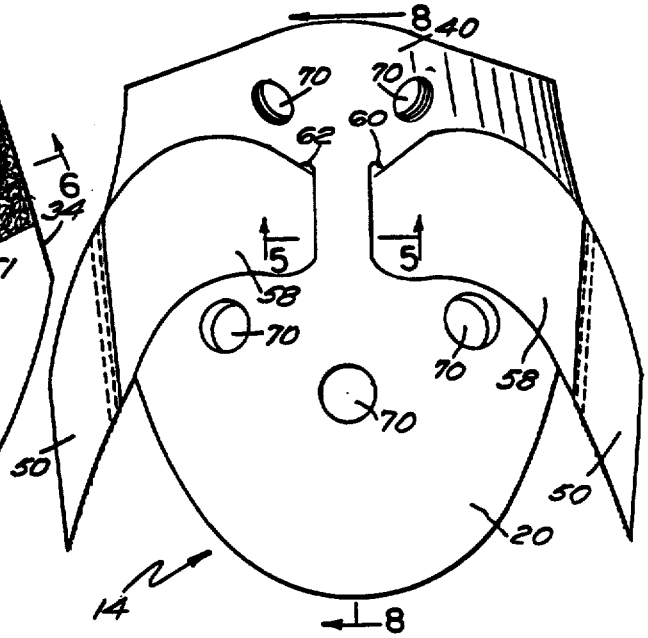
FIG. 4 is a perspective view of the back half of the collar as viewed from the back.
Figure 7:
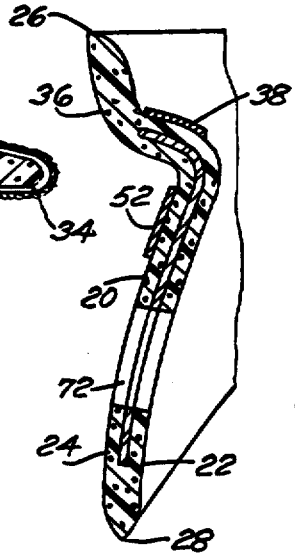
FIG. 7 is a sectional view of the front half of the collar along lines 7—7 of FIG. 3.
Figure 8:
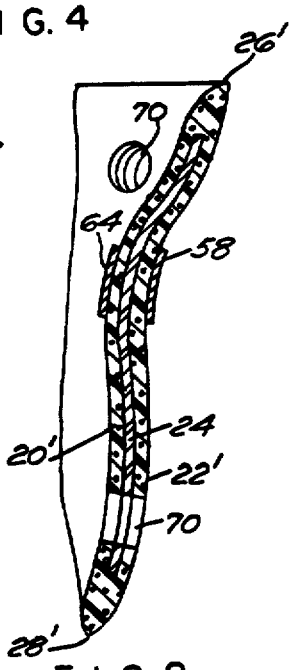
FIG. 8 is a sectional view of the back half of the collar as seen along the lines 8—8 of FIG. 4.

With reference to the drawings, the cervical collar 10 includes a front half 12, a back half 14 and a releasable strap means 16. The front and back halves 12, 14, are provided in a laminate or sandwich construction including the outer layers 20, 22 and the inner layer 24 as best seen in FIGS. 5, 6, 7 and 8. The material of the outer layers 20, 20', 22, 22' is a foam polymeric material such as, for example, polyethylene or polyurethane. The foam material is preferably soft and pliable for comfort, yet tear resistant for durability. A suitable commercially available foam material is foam polyethylene sheet sold by Voltex under the trade designation Volara 4E3/16.

The material of the inner layer 24 is a semirigid or rigid sheet of a solid thermoplastic material such as, for example, a LDPE or LLDPE polyethylene or high density polypropylene. A suitable commercially available solid material is 100 mil LDPE sheet sold by Bisby Co., Portsmouth, NH.

The inner layer 24 is substantially coextensive with the outer layers 20, 22 except for the edges 26, 28, 26', 28' of each half 12, 14 respectively, of the collar 10. This results in an unreinforced or padded periphery of about 5–20 mm along the edges 26, 26', 28, 28' of each half 12, 14 for comfort at the points of contact with the head, neck, shoulders, etc. As seen from FIG. 6, reinforcing layer 24 also stops short of the ends of the collar halves, such that the ends are flexible and in the case of the front half, short of the stitching 56 fastening the straps to the collar half.

The front half 12 is generally U-shaped, is wider at the front most portion 30 and tapers both in height and in thickness toward the ends 32, 34 which correspond to the respective sides of the head and neck. The front most portion 30 has a depression 36 formed in the top edge thereof to receive and support the chin. If desired, additional padding may be provided in the chin depression 36 in the form of moleskin or flannel pad 38 which may be glued or otherwise secured in the depression 36. The front most portion extends downwardly from the top edge to a bottom edge 28 that engages the chest of the user.

The back half 14 is generally U-shaped, is widest at the rearmost portion 40 and tapers both in height and in thickness toward the ends 42, 44 which correspond to the respective sides of the head and neck. The rearmost portion 40 is curved in the vertical direction to correspond to the shape of the base of the head and neck along the spine.

The front and back halves 12, 14 are secured in place on the neck by releasable strap means 16. The ends 32, 34 of the front half 12 overlap the respective ends 42, 44 of the back half 14 to provide continuous encircling support around the entire neck inhibiting side-to-side movement of the head. Forward motion of the head is restricted by the front most portion 30 of the front half 12 which prevents downward movement of the chin by transmitting force from the chin depression 36 to the bottom of the front most portion 30 in contact with the upper portion of the chest along the clavicles and the sternal notch. Rearward movement of the head is restricted by the rearmost portion 40 of the back half 14 which transmits force from the base of the head at the top of the rearmost portion 40 to the bottom of the rear portion 40 in contact with the upper part of the back and shoulders along the trapezius muscles and the spine.

Releasable strap means 16 is preferably a hook and loop fabric fastener comprising hook attachment material 50 and loop receiving material 51 sold under the trademark Velcro but alternatively and less preferably could be buckles, snaps, buttons, or the like. In the preferred embodiment, the strap 16 portion 52 spans the outer perimeter of the front half 12 and is securely fastened thereto at the ends 32, 34 by stitching 54, 56 or other suitable fastening means. A second portion 58 spans the outer perimeter of the back half 14, being looped through parallel slots 60, 62. The second portion 58 is generally of uniform width exceeding the length of the slots 60, 62 and has a narrow portion 64 corresponding to the slots 60, 62. The narrow portion 64 has a width equal to or less than the length of the slots 60, 62. The second portion of the strap 16 is prevented from slipping with respect to the back portion 14 by means of its generally uniform width exceeding the length of the parallel slots 60, 62 through which it is looped.

Figure 6:
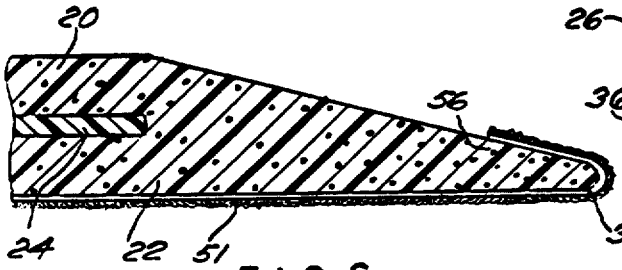
FIG. 6 is a sectional view of a portion of the strap as secured to the front half of the collar along the lines 6—6 in FIG. 3.
Figure 6A:
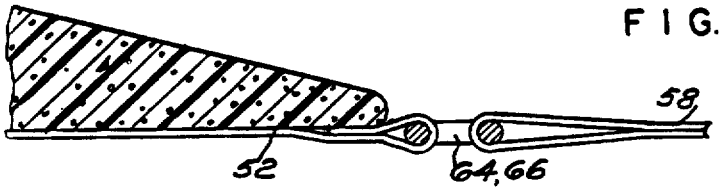
FIG. 6A is a sectional view of a portion of the front half of a modified collar securing strap.

Preferably, a loop fabric 51 is affixed to the strap portion 52 and the strap portion 58 has terminal ends with hook fabric 50. Alternately, buckles 64, 66 (see FIG. 6A) may be attached to each end of the first strap portion 52 by looping the ends of the portion 52 through the respective buckles 64, 66 and doubling them over at the stitching 54, 56. The ends of the second strap portion 58 can then be looped through the respective buckles 64, 66 and doubled over to mate the surfaces such as 50, 51, thereby securing the collar in place.

A plurality of perforations 70 may be formed in the front and back halves 12, 14 to permit ventilation. In addition, a large hole 72 may be formed in the front half 12 at the front portion 30 to correspond to and accommodate the enlarged portion of the trachea at the base of the neck for added comfort. This is a distinct advantage over the collar of U.S. Pat. No. 3,756,226 because the external reinforcement of that collar at the bight prevents any such accommodation of the Adam's apple and instead presses tightly against it.

The manufacture of the present collar is simple and economical. The layers, 20, 22, 24 are cut to shape from a sheet of the respective materials for the front and back halves 12, 14. The sheets are then placed in their respective positions and heated sufficiently to form the laminate by bonding or fusing of the opposing surfaces of the inner layer 24 to the adjacent surfaces of the opposing surfaces of the inner layer 24 to the adjacent surfaces of the outer layers 20, 22 and by bonding or fusing of the opposing surfaces of the outer layer 20 and the outer layer 22 at the edges 26, 28. The parallel slots 60, 62, and if desired, the air holes 70 and the trachea hole 72, are then cut in the laminate. The laminate is then heated above its glass transition temperature and formed into the appropriate shape by compression molding, cooled in the mold and then removed. The edges are then trimmed and the strap 16 attached by stitching to the front half 12 and looping through the parallel slots 60, 62 on the back half 14.

The collar may be made available in various sizes of height and diameter to accommodate varying sizes of necks, ranging from heights of 3 to 6 inches and internal diameters 3¼, 4¼ and 5¼ inches and diameters 9½, 10, ½, and 12½ inches will provide 9 standard sizes which will comfortable and supportively fit most any neck.

We claim:

1. A cervical collar comprising:

front and back halves adapted to fit around a person's neck;

said halves being preformed from a laminated member comprising exterior layers of foamed polymeric material and an interior layer disposed between said exterior layers, said [internal] *interior* layer being of a substantially solid thermoplastic material and being centrally coextensive with the exterior layers to define an un-reinforced periphery;

said front half having a front most portion with a chin receiving depression formed in the top edge thereof, said portion extending generally downwardly and providing a lower edge means for engaging the upper portion of the chest, and end portions extending from said front most portion along both sides of the neck, said end portions tapering in height away from said front portion;

said [rear] *back* half having a rear most portion curved in the vertical direction to correspond to the shape of the base of the head and neck along the spine, and end portions extending from said rear most portion along both sides of the neck, said end portions tapering in height away from said rear most portion, said rear portion having a pair of parallel slots substantially central of the rear half;

said halves being provided with a plurality of ventilation holes;

said [ends] *end portions* of said front half tapering in thickness so as to overlap said [ends] *end portions* of said back half to provide continuous encircling support around the neck;

strap means *having first and second ends* for positioning said halves on the neck and strap securing means being mutually cooperative for releasably securing the ends of said strap means and retaining said halves in a collar configuration;

said strap means including a first strap spanning said front half along its outer perimeter and securely fastened thereto [at intermediate points] *adjacent*

*the end portions of said front half* and at said [ends] *end portions of said front half* by stitching to the front half *in the strap securing means*, and a second strap spanning said back half along its outer perimeter by being looped through parallel slots formed in said rear most portions, said second strap being gripped by said slots.

* * * * *